United States Patent
Matthews et al.

(10) Patent No.: US 11,284,837 B1
(45) Date of Patent: Mar. 29, 2022

(54) WEARABLE CHILD-MONITOR SYSTEM INCLUDING SECURITY SCREW AND BREAKAWAY

(71) Applicant: KB, LLC, Owasso, OK (US)

(72) Inventors: Christie Matthews, Tulsa, OK (US); Tim Thornton, Broken Arrow, OK (US)

(73) Assignee: KB, LLC, Tulsa, OK (US)

( * ) Notice: Subject to any disclaimer, the term of this patent is extended or adjusted under 35 U.S.C. 154(b) by 0 days.

(21) Appl. No.: 16/838,758

(22) Filed: Apr. 2, 2020

Related U.S. Application Data

(60) Provisional application No. 62/828,265, filed on Apr. 2, 2019.

(51) Int. Cl.
  *G08B 21/02* (2006.01)
  *A44C 5/00* (2006.01)
  *A61B 5/00* (2006.01)
  *G06F 1/16* (2006.01)
  *G08B 25/10* (2006.01)

(52) U.S. Cl.
  CPC ............ *A61B 5/681* (2013.01); *A44C 5/0007* (2013.01); *G08B 21/0205* (2013.01); *G08B 21/0288* (2013.01); *G06F 1/163* (2013.01); *G08B 25/10* (2013.01)

(58) Field of Classification Search
  None
  See application file for complete search history.

(56) References Cited

U.S. PATENT DOCUMENTS

| | | | | |
|---|---|---|---|---|
| 5,978,493 A * | 11/1999 | Kravitz | ............... | G09F 3/005 382/115 |
| 6,195,009 B1 * | 2/2001 | Irizarry | ............. | G08B 13/2422 340/551 |
| 7,106,191 B1 * | 9/2006 | Liberati | ............. | G08B 21/0286 340/539.15 |
| 7,696,887 B1 * | 4/2010 | Echavarria | ......... | G08B 21/0247 340/573.1 |
| 8,648,721 B2 * | 2/2014 | Copeland | ........... | G08B 13/2431 340/571 |
| 8,741,410 B2 * | 6/2014 | Cattacin | ................. | B65H 31/10 428/43 |
| 10,372,164 B2 * | 8/2019 | Huitema | ............. | G06F 3/04845 |
| 10,702,029 B2 * | 7/2020 | Herz | .................... | A44C 5/0053 |
| 2002/0024212 A1 * | 2/2002 | Malleis | ................. | A63C 11/00 280/809 |
| 2003/0030561 A1 * | 2/2003 | Yafuso | ............... | G08B 21/0286 340/573.4 |

(Continued)

*Primary Examiner* — Muhammad Adnan
(74) *Attorney, Agent, or Firm* — GableGotwals

(57) ABSTRACT

Embodiments of a personal safety monitoring system this disclosure include a wristband that includes a two-way security screw having a non-standard drive recess and sized for insertion into adjustment holes of the wristband; a security key having a non-standard drive configured for insertion into the non-standard drive recess of the two-way security screw; and a designed fail point located along at least one of the first and second lengths of the wristband, the designed fail point configured to fail at a predetermined pull force on the wristband. A monitor may receive signals from the wristband and sound an alert when the wristband exceeds a maximum allowable distance from the monitor.

9 Claims, 7 Drawing Sheets

(56) References Cited

U.S. PATENT DOCUMENTS

| | | | | |
|---|---|---|---|---|
| 2005/0280546 A1* | 12/2005 | Ganley | G08B 13/1427 | 340/573.4 |
| 2006/0081665 A1* | 4/2006 | Nguyen | A63H 27/10 | 224/267 |
| 2006/0162208 A1* | 7/2006 | Ciarrocchi | G09F 3/005 | 40/633 |
| 2006/0176183 A1* | 8/2006 | Jetton | G08B 21/0288 | 340/573.1 |
| 2006/0232429 A1* | 10/2006 | Gonzalez | G08B 21/0252 | 340/573.1 |
| 2006/0250255 A1* | 11/2006 | Flanagan | G08B 21/0208 | 340/573.4 |
| 2007/0182548 A1* | 8/2007 | Raad | G08B 21/0269 | 340/539.13 |
| 2008/0088597 A1* | 4/2008 | Prest | G06F 3/0338 | 345/173 |
| 2009/0040053 A1* | 2/2009 | White | G08B 21/0288 | 340/573.4 |
| 2010/0231378 A1* | 9/2010 | Ward | A61B 5/1112 | 340/539.11 |
| 2010/0267361 A1* | 10/2010 | Sullivan | H04W 4/02 | 455/404.2 |
| 2012/0203076 A1* | 8/2012 | Fatta | A61B 5/681 | 600/300 |
| 2013/0063268 A1* | 3/2013 | Golomb | G08B 21/0294 | 340/573.4 |
| 2013/0083496 A1* | 4/2013 | Franklin | G09G 3/2092 | 361/749 |
| 2013/0157655 A1* | 6/2013 | Smith, II | H04M 1/72427 | 455/426.1 |
| 2013/0197680 A1* | 8/2013 | Cobbett | A61B 5/681 | 700/91 |
| 2013/0309963 A1* | 11/2013 | Shasha | H04M 1/7243 | 455/39 |
| 2014/0124389 A1* | 5/2014 | Borlenghi | G08B 21/0269 | 206/37 |
| 2015/0187197 A1* | 7/2015 | Golomb | G08B 21/0294 | 340/686.1 |
| 2018/0025605 A1* | 1/2018 | Thomas | G07C 9/257 | 455/90.1 |
| 2019/0208363 A1* | 7/2019 | Shapiro | G16H 50/30 | |

* cited by examiner

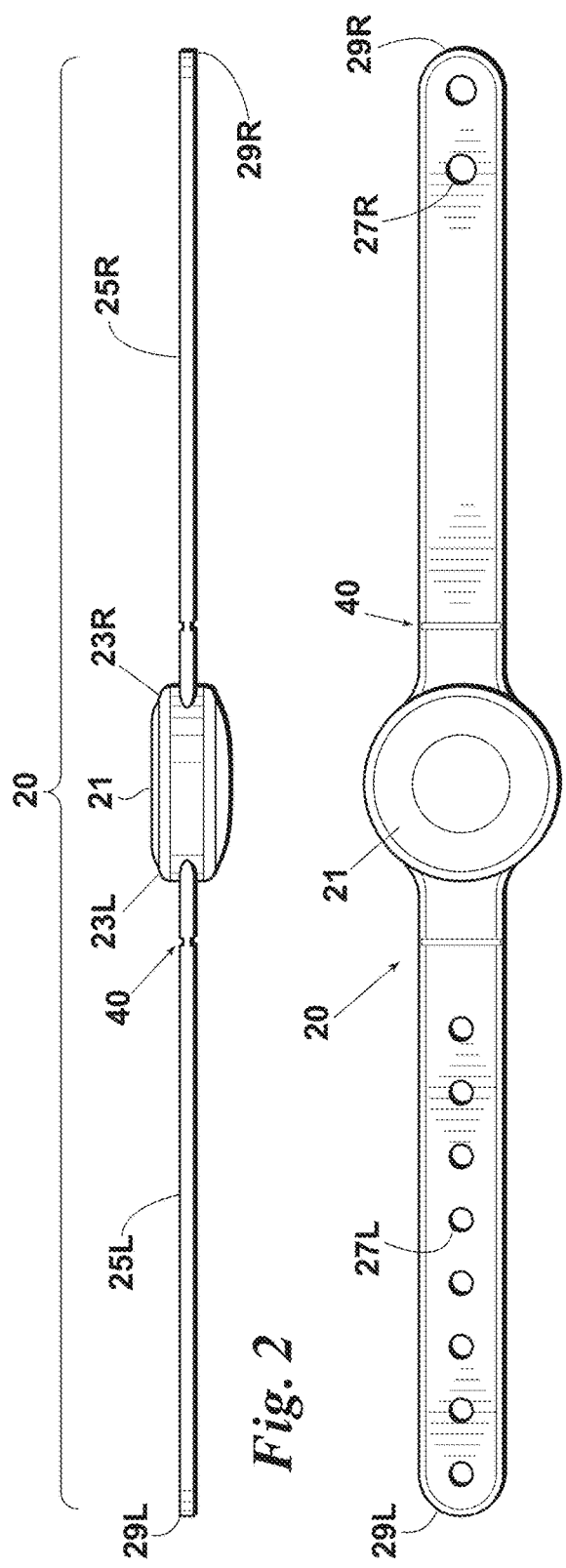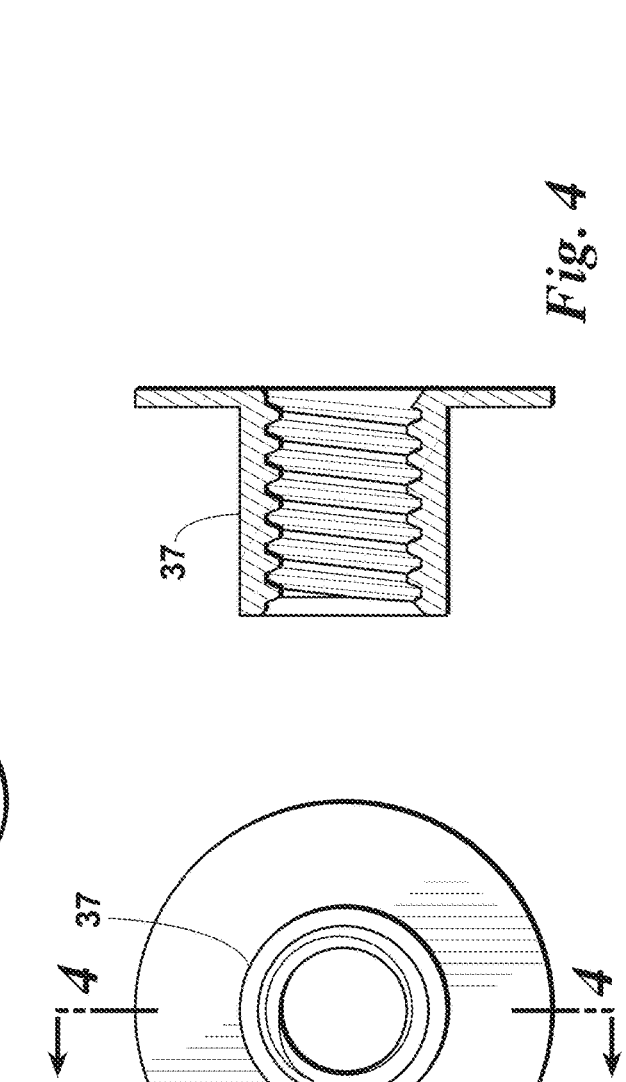

WEARABLE CHILD-MONITOR SYSTEM INCLUDING SECURITY SCREW AND BREAKAWAY

CROSS-REFERENCE TO CO-PENDING APPLICATIONS

This application claims priority to U.S. Provisional Application No. 62/828,265, filed Apr. 2, 2019, the entire application is incorporated herein by reference.

BACKGROUND

This disclosure is in the field of monitoring systems and, more specifically, to systems and methods for monitoring a wearable monitor system such as a wristband.

SUMMARY

Embodiments of a personal monitoring system of this disclosure comprise a wristband including a first mobile device configured for communication with a second mobile device, a device holding end, a plurality of size-adjustment holes, a designed fail point located between the first mobile device holding end and a nearest size-adjustment hole to that end; a security screw sized to be received by a respective size-adjustment hole of the plurality of size-adjustment holes; and a security key configured to engage a drive of the security screw. The second mobile device monitors a condition of the first mobile device and, when the condition falls outside a predetermined limit, triggers an alert.

Embodiments of a monitored wristband of this disclosure may be configured for use with a personal safety monitoring system, the monitored wristband including: a first mobile device connected to the monitored wristband and containing communication means; a first band adjustment hole located along a first length of the monitored wristband between the puck and a first tail end of the monitored wristband; a second band adjustment hole located along a second length of the monitored wristband between the puck and a second tail end of the monitored wristband; a two-way security screw including a non-standard drive recess and sized for insertion into the first and second band adjustment holes; a security key including a non-standard drive configured for insertion into the non-standard drive recess of the two-way security screw; and a designed fail point located along at least one of the first and second lengths of the monitored wristband, the designed fail point configured to fail at a predetermined pull force on the monitored wristband.

In embodiments, the designed fail point may include or contain a circuitry of the monitored wristband, the circuitry configured to trigger an alert condition upon a failure of the designed fail point. The designed fail point may have a thickness different than that of the first and second lengths of the monitored wristband. The designed fail point may run widthwise relative to the first and second lengths. In some embodiments, the monitored wristband may include one or more environmental sensors housed within the first mobile device, the first length, or the second length (or some combination thereof). The one or more environmental sensors may include a water sensor.

The monitored wrist band may be used in conjunction with a monitor including a second mobile device containing communication means; the monitor configured to receive an alert when the monitored wristband experiences a predetermined alert condition. The monitor may be configured to control an on-off state of the one or more environmental sensors. The predetermined alert condition may be a break in the circuitry of the monitored wristband, a maximum physical distance between said wristbands, a minimum battery power level of one of said wristbands, a maximum amount of time the one or more environmental sensors is detecting an undesirable environmental condition.

BRIEF DESCRIPTION OF THE DRAWINGS

FIG. 1 is a side elevation view of an embodiment of a monitored wristband of this disclosure. The band may be secured using a security screw (se e.g., FIGS. 3-7). The band may include a weakened section to provide for breakaway.

FIG. 2 is a front elevation view of the wristband.

FIG. 3 is top plan view of a female nut configured for insertion into a hole of the wristband.

FIG. 4 is a view taken along section line 4-4 of FIG. 3.

FIG. 10A is an embodiment of a mobile device of this disclosure. The mobile device may be a smart watch or a cell phone including software configured to monitor the wristband.

DEFINITIONS

Figure 5:
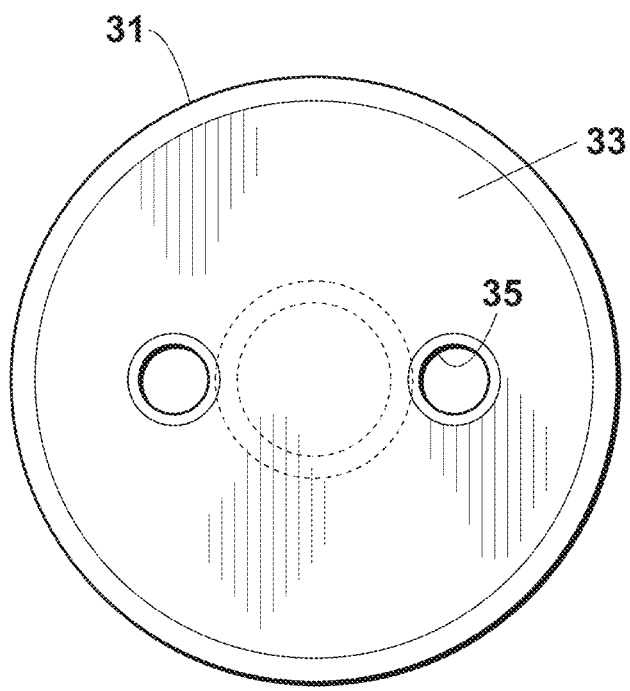
FIG. 5 is a front elevation view of an embodiment of a security screw of this disclosure. The security screw may be a male spanner screw configured for connection to the female nut.
Figure 6:
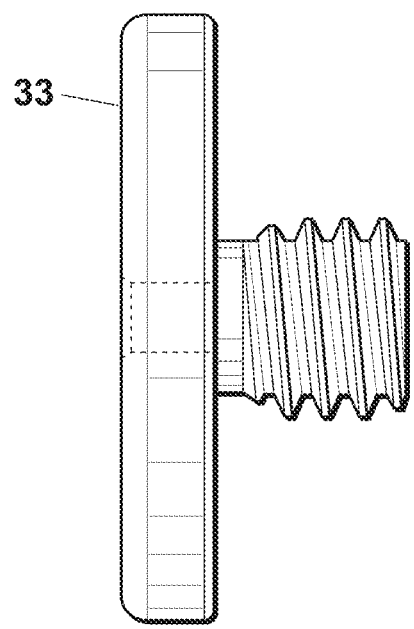
FIG. 6 is a side elevation view of the male spanner screw.
Figure 7:
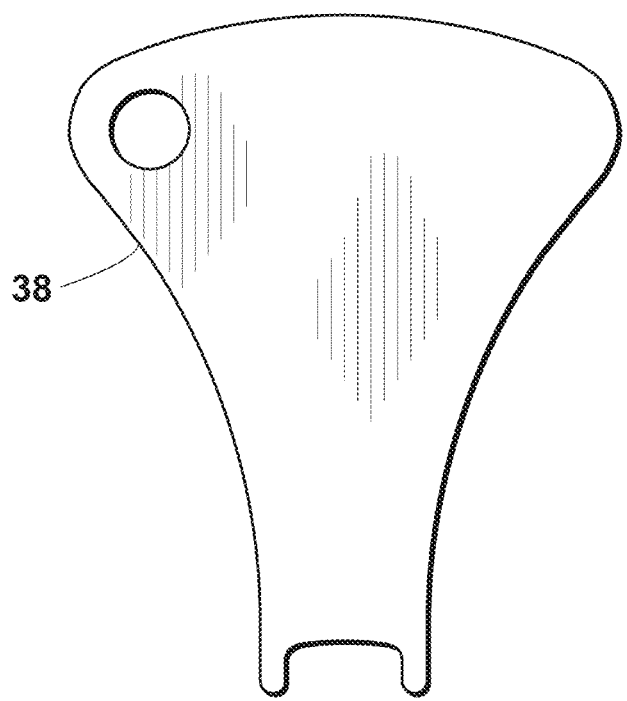
FIG. 7 is a front elevation view of the spanner tool configured to fasten the male spanner screw.
Figure 8:
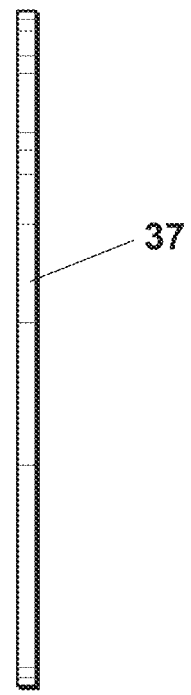
FIG. 8 is a side elevation view of the spanner tool.
Figure 9:
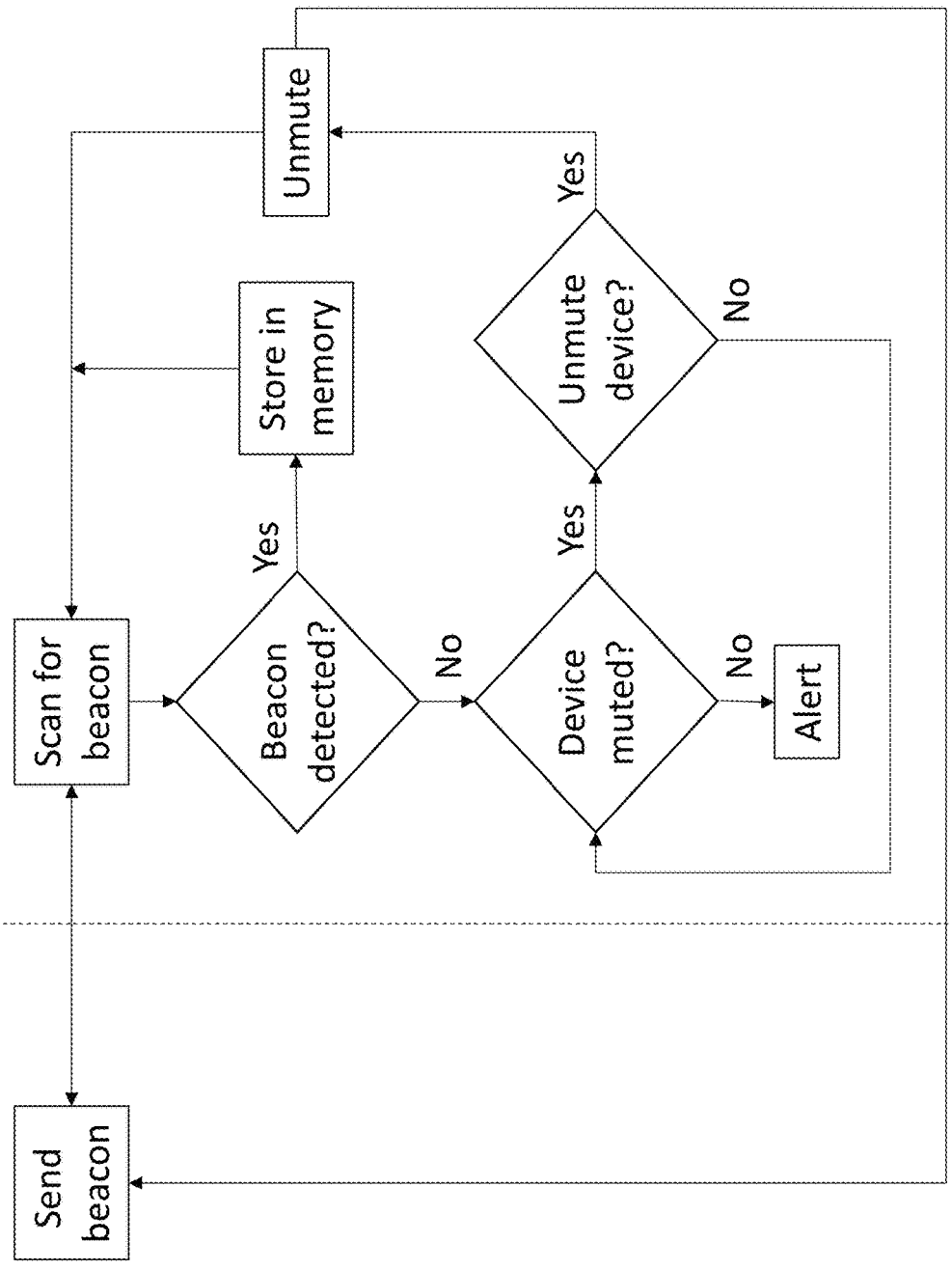
FIG. 9 is a flow chart illustrating an embodiment of a monitoring method of this disclosure. The monitoring device may be a mobile device with associated software. The mobile device may a smart watch (see e.g.
Figure 10B:
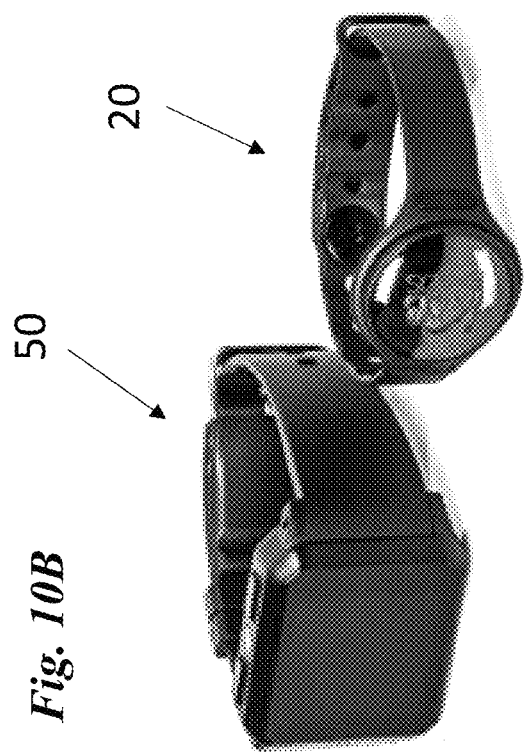
FIG. 10B is the mobile device of FIG. 10 when paired to a monitored wristband of this disclosure.
Figure 10A:
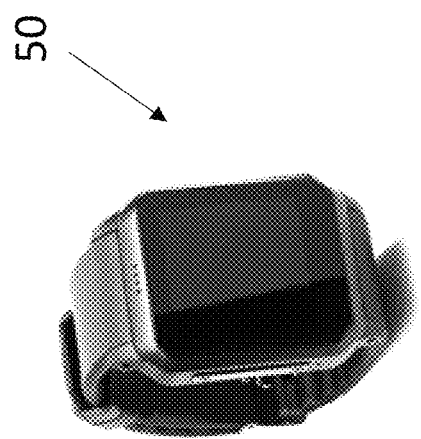
FIG. 10A).
Figure 10C:
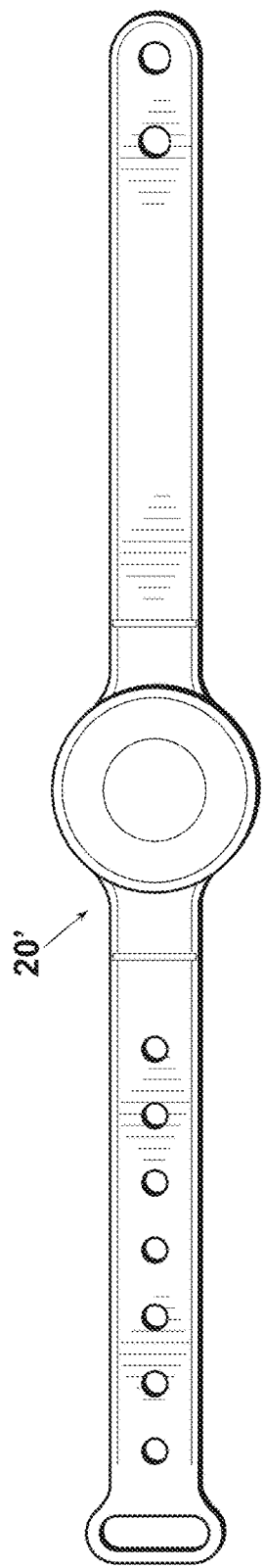
FIG. 10C is an embodiment of the monitored wrist band of FIG. 10B.
Figure 14:
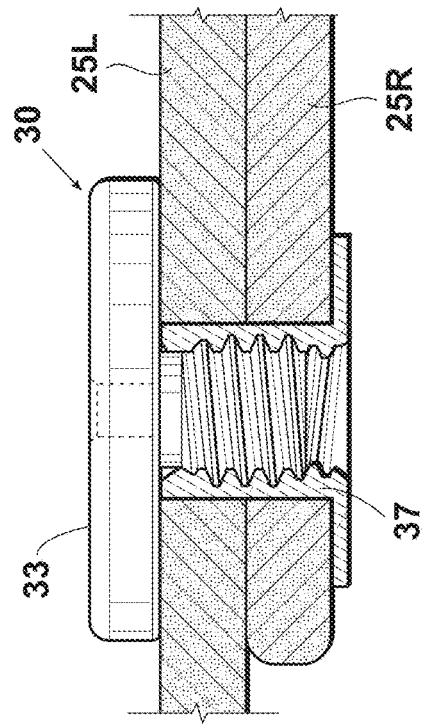
FIG. 14 is an assembled view of the security screw of FIG. 13.
Figure 13:
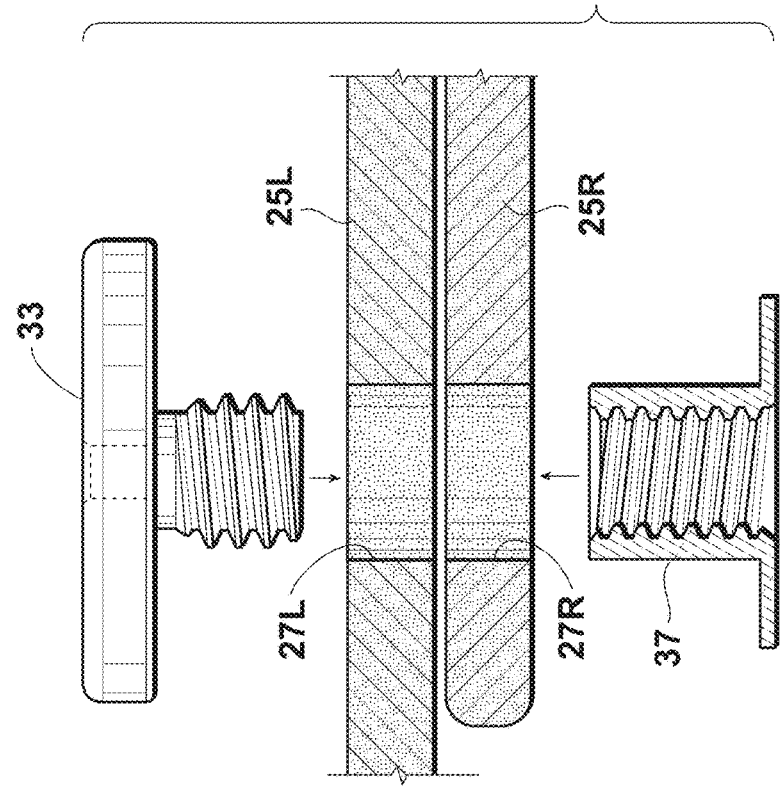
FIG. 13 is an exploded assembly view showing an embodiment of the security screw relative to the band.
Figure 11:
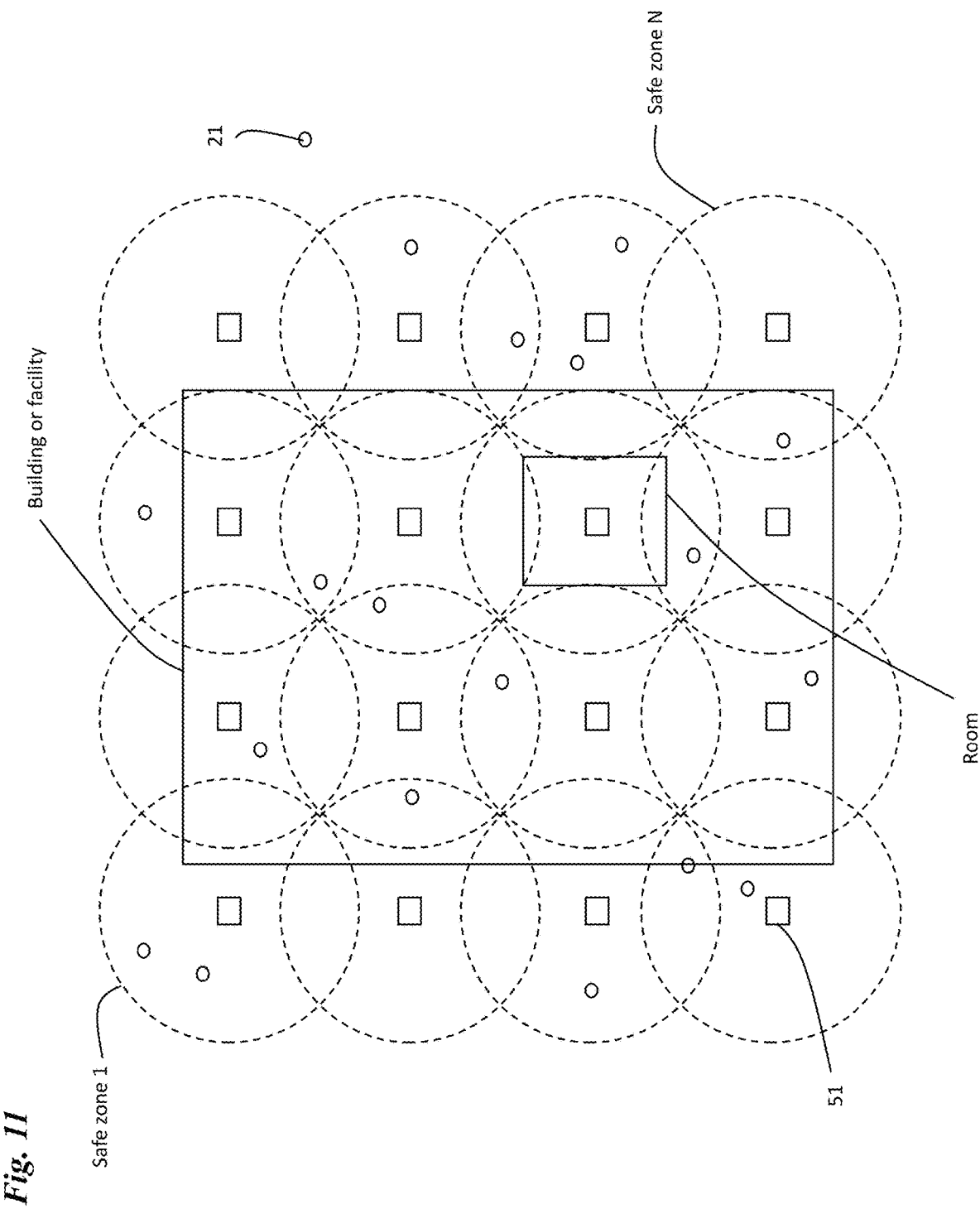
FIG. 11 is a schematic of an embodiment in which multiple monitoring devices are placed about a building or facility such as, but not limited to, a school campus or hospital, to monitor occupants with an alert occurring when an occupant wanders outside one or more predetermined safe zones.
Figure 12:
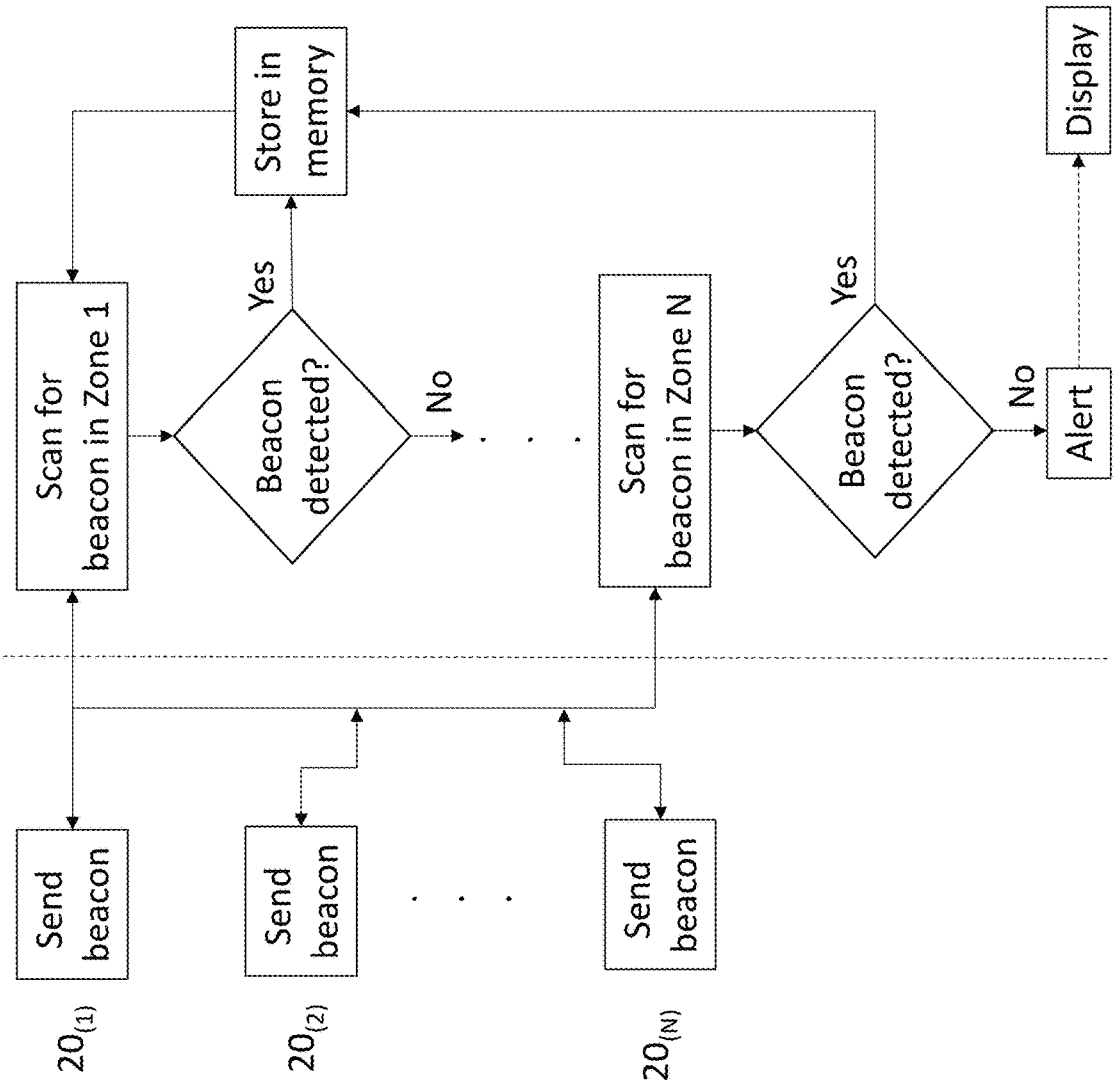
FIG. 12 is a flow chart illustrating an embodiment of a monitoring method for use in a building or facility.

For the purposes of this disclosure, the following definitions apply:

Designed fail point—a weakened portion of a band, made of the same material as the band, and located entirely between a device holding end of the band and a tail end of the band. The weakened portion breaks at a predetermined pull force on the band that is less than the pull force required to break adjacent portions of the band. An adjustment hole of the band, by itself, is not a designed fail point. However, the designed fail point may include an adjustment hole and a portion of the band adjacent to the adjustment hole.

Mobile device—a portable computing device including hardware and software configured for RFID communication with another mobile device.

Device holding end—the end of the wristband that connects to a mobile device, such as a puck, that contains the hardware and software.

Security screw—a fastener including a drive or recess in the fastener head that cannot be mated with a standard screw drive tool (e.g. pozi, Phillips, slotted, star, or socket key) but requires either a modification to a standard drive tool a non-standard drive tool. A security screw of this disclosure is a two-way security screw.

DETAILED DESCRIPTION

Embodiments of a personal safety monitoring system 10 of this disclosure include a monitored wristband 20 including a first mobile device 21 configured for communication with a second mobile device 51. The wristband 20, which may be made of rubber or plastic, includes a security screw 30 and a designed fail point 40. The first mobile device 21 is connected to a respective device holding end 23L, 23R of a first and second length 25L, 25R of the wristband 20. In some embodiments, the first mobile device 21 may be a puck-shaped housing containing computer hardware, associated software, and communication means. The housing may be water resistant. The communication means may include RFID transmitting and receiving means.

In embodiments, the first or second length 25L, 25R may include or contain a portion of the circuitry of the monitored wristband 20, with the circuitry running through the designed fail point 40. The circuitry is configured to trigger an alert condition upon a failure of the designed fail point 40. Regardless of whether it includes circuitry, the designed fail point may have a thickness different than that of the first and second lengths 25L, 25R of the monitored wristband 20. The designed fail point 40 may run widthwise relative to the first and second lengths 25L, 25R. The designed fail point 40 may be located between adjacent adjustment holes 27L, 27R or may include an adjustment hole 27L, 27R.

The security screw 30 may be any type of two-way security screw suitable and sized for insertion into a size-adjustment hole 27L, 27R of the wristband 20. In some embodiments, the security screw 30 is a spanner screw 31 received by a complementary nut 37. The screw 31 may include a head 33 containing a non-standard drive tool receiving recess 35. A security key 38 containing a non-standard drive tool or bit 39 and configured for use with the security screw 30 may be used to tighten and loosen the screw 30.

In embodiments, the fail point 40 is located between the device holding end 23L or 23R of the wristband 20 and the nearest adjustment hole 27L or 27R. In other embodiments, the fail point 40 is located between the device holding end 23L or 23R and a respective tail end 29L or 29R of the band 20. The fail point 40 may be configured to break the wristband 20 at a predetermined pull force. In some embodiments, the fail point 40 includes a serrated or perforated line extending an entire width of the band 20. The fail point 40 may be configured to break a circuitry of the monitored wristband 20 and trigger an alert condition. The band 20 may be thinner at the fail point 40 than at other locations along the first and second lengths 25L, 25R.

In embodiments, the monitoring device 50 is a second mobile device 51 configured to scan for a condition of the first mobile device 21 and sound an alert on the monitoring device 50 when the second mobile device 51 detects a predetermined alert condition. The second mobile device 51 may be a smart phone or smart watch. The second mobile device 51, like the first mobile device 21, may include RFID transmitting and receiving means. In some embodiments, the second mobile device 51 may be configured to turn the first mobile device 21 off/on. The second mobile device 51 may be able to suspend monitoring or suspend signal broadcasting by the first mobile device 21. One or both mobile devices 21, 51 may include a test circuit configured to continuously or intermittently test at least one function of the device 21, 51. In some embodiments, the second mobile device 51 may be a tower or table top unit arranged about or within a building or facility. For example, the second mobile device 51 may be configured to monitor a predetermined perimeter about the building or a room(s) within the building.

The first mobile device 21 may be synchronized with the second mobile device 51 when first used and placed next to, or in close proximity to, one another. Because the first mobile device 21 is receiving or sending a unique signal, and because the second mobile device 51 is sending or scanning for the presence of that unique signal, communication between the synchronized bands should not be interfered with by other signals or bands.

The predetermined alert condition may be an out-of-range condition such as a maximum physical distance between the first and second mobile devices 21, 51 (e.g. a "safe zone"). The alert condition may also include a minimum battery power level, a break in a circuitry of the monitored wristband such as when the fail point breaks, a maximum amount of time the wristband remains stationary, or a scheduled test of the wristband. The alert, which may be configured for either or both mobile devices, may be a sound, a vibration, or both a sound and a vibration.

In some embodiments, the monitored wristband 20 may further include one or more environmental sensors S. The one or more environmental sensors S may include a water sensor. The second mobile device 51 may be configured to control an on-off state of the one or more environmental sensors S. The predetermined alert condition may be a maximum amount of time the one or more environmental sensors S is detecting an undesirable environmental condition.

While example embodiments have been described, the following claims define the scope of the invention. The claims include the full range of equivalents to which each recited element is entitled.

What is claimed:

1. A monitored wristband configured for use with a personal safety monitoring system, the monitored wristband comprising:
   a first mobile device including a puck connected to the monitored wristband and containing communication means, a water sensor, and a battery power level indicator;
   a first band adjustment hole located along a first length of the monitored wristband between the puck and a first tail end of the monitored wristband;
   a second band adjustment hole located along a second length of the monitored wristband between the puck and a second tail end of the monitored wristband;
   a spanner screw including a pair of spanner drive recesses and a complementary nut sized for insertion into the first and second band adjustment holes; and
   a designed fail point located along each of the first and second lengths of the monitored wristband, the designed fail point configured to break a corresponding one of the first and second lengths in response to a predetermined pull force on the monitored wristband;
   the designed fail point, containing a circuitry of the monitored wristband, running widthwise relative to the first and second lengths, extending an entire width of a corresponding one of the first and second lengths, and having a thickness along the entire width less than that of the first and second lengths of the monitored wristband;

wherein the monitored wrist band, when secured about a wrist of a user by the spanner screw and the complementary nut, is removable only by a spanner tool including a pair of driver bits or a pull force greater than the predetermined pull force; and wherein the monitored wrist band activates an alert upon a break in the circuitry through the designed fail point.

2. The monitored wristband of claim 1, wherein the monitored wristband is in communication with a monitor including a second mobile device containing communication means; the monitor configured to receive the alert, and wherein the maximum predetermined physical distance being relative to the monitor.

3. The monitored wristband of claim 1, wherein the designed fail point is located between, and adjacent to, a corresponding one of the first and second adjustment holes and the puck.

4. The monitored wrist band of claim 1, wherein the designed fail point includes a serration or a perforation.

5. A personal safety monitoring system comprising:
a monitored wrist band including:
- a first mobile device connected to the monitored wristband and containing communication means;
- a first band adjustment hole located along a first length of the monitored wristband between the first mobile device and a first tail end of the monitored wristband;
- a second band adjustment hole located along a second length of the monitored wristband between the first mobile device and a second tail end of the monitored wristband;
- a security spanner screw including a pair of spanner drive recesses and a complementary nut sized for insertion into the first and second band adjustment holes; and
- a designed fail point, containing a circuitry of the monitored wristband, located along each of the first and second lengths of the monitored wristband between, and adjacent to, a corresponding one of the first and second adjustment holes and the first mobile device, the designed fail point running widthwise relative to the first and second lengths, extending an entire width of a corresponding one of the first and second lengths, and having a thickness along the entire width less than that of the first and second lengths and configured to break a corresponding one of the first and second lengths of the monitored wristband at a predetermined pull force on the monitored wristband;

a spanner tool including a pair of spanner drive bits configured for insertion into the pair of spanner drive recesses of the spanner screw; and a monitor including a second mobile device containing communication means; the monitor configured to receive an alert when the monitored wristband experiences a predetermined alert condition;

wherein the monitored wrist band, when secured about a wrist of a user by the spanner screw and complementary nut, is removable only by the spanner tool or a pull force greater than the predetermined pull force; and wherein the monitored wrist band activates the alert upon a break in the circuitry through the designed fail point.

6. The personal safety monitoring system of claim 5, further comprising:
the monitored wristband including one or more environmental sensors housed within at least one of the first mobile device, the first length, and the second length.

7. The personal safety monitoring system of claim 6, the monitor configured to control an on-off state of the one or more environmental sensors.

8. The personal safety monitoring system of claim 6, wherein, a second predetermined alert condition is a condition when the one or more environmental sensors are detecting an undesirable environmental condition for an amount of time.

9. The personal safety monitoring system of claim 5, wherein the designed fail point includes a serration or a perforation.

* * * * *